United States Patent
Inglese (10) Patent No.: US 7,711,173 B2
(45) Date of Patent: May 4, 2010

(54) SIGNAL PROCESSING METHOD IN A DENTAL RADIOLOGY APPARATUS

(75) Inventor: Jean-Marc Inglese, Bussy Saint Georges (FR)

(73) Assignee: Carestream Health, Inc., Rochester, NY (US)

( * ) Notice: Subject to any disclaimer, the term of this patent is extended or adjusted under 35 U.S.C. 154(b) by 1013 days.

(21) Appl. No.: 10/595,985

(22) PCT Filed: Nov. 13, 2004

(86) PCT No.: PCT/EP2004/012886

§ 371 (c)(1),
(2), (4) Date: May 24, 2006

(87) PCT Pub. No.: WO2005/051200

PCT Pub. Date: Jun. 9, 2005

(65) Prior Publication Data

US 2007/0126752 A1    Jun. 7, 2007

(30) Foreign Application Priority Data

Nov. 26, 2003    (EP) ................... 03292945

(51) Int. Cl.
*G06K 9/00* (2006.01)
*G09G 5/02* (2006.01)

(52) U.S. Cl. ...................... 382/132; 345/589

(58) Field of Classification Search .......... 382/128, 382/129, 130, 131, 132, 133, 134; 378/46, 378/62, 90, 92, 98.7, 98.8, 98.9, 98.12, 165, 378/175, 38, 98.6, 101, 138, 191, 901; 250/58, 250/581, 363.04, 370.09; 601/162; 433/68, 433/201.1

See application file for complete search history.

(56) References Cited

U.S. PATENT DOCUMENTS

| | | | |
|---|---|---|---|
| 5,663,998 A * | 9/1997 | Suzuki et al. | 378/62 |
| 5,912,942 A * | 6/1999 | Schick et al. | 378/98.8 |
| 5,970,164 A * | 10/1999 | Bamberger et al. | 382/128 |
| 6,047,043 A * | 4/2000 | Kamps | 378/98.7 |
| 6,359,628 B1 * | 3/2002 | Buytaert | 345/619 |
| 6,454,460 B1 * | 9/2002 | Ramanathan et al. | 378/207 |

FOREIGN PATENT DOCUMENTS

| | | |
|---|---|---|
| EP | 0 224 956 | 11/1986 |
| EP | 0 129 451 | 12/1987 |
| EP | 0 639 819 | 8/1993 |
| EP | 0 772 158 | 10/1996 |
| FR | 547495 | 5/1921 |
| FR | 2 750 821 | 7/1996 |

* cited by examiner

*Primary Examiner*—Abolfazl Tabatabai (57) ABSTRACT

The application relates to a signal processing method in a dental radiology apparatus comprising an intraoral sensor that delivers at least one analog image output signal in response to an exposure of said sensor to x-rays, characterized in that it includes the following steps: conversion of said at least one analog image output signal into one digital image output signal, processing of the digital image output signal to obtain a report indicating the x-ray exposure level that has been used to deliver said analog output signal, the report indicating the exposure level corresponding to an exposure level classified as under-exposure, correct exposure or over-exposure, supply of the report indicating the exposure level used.

51 Claims, 3 Drawing Sheets

SIGNAL PROCESSING METHOD IN A DENTAL RADIOLOGY APPARATUS

FIELD OF THE INVENTION

The invention relates to the field of dental radiology.

BACKGROUND OF THE INVENTION

Dental radiology equipment as described in French patent No. 547,495 and European patent No. 0,129,451 is known.

Such equipment comprises an x-ray source that emits radiation directed to a tooth located in a patient's mouth and behind which is an intraoral sensor that receives the x-rays that have passed through the tooth.

This sensor comprises:
- a scintillator on entry to convert the x-rays that have passed through the tooth into visible radiation,
- a fiber optic plate to transmit the converted visible light to a charge-coupled device (CCD) type detector, which reconverts the converted visible light into an analog electrical signal, while absorbing the residual x-rays that have not been converted into visible light.

The electrical signal is amplified and transmitted in analog form through a long cable, to a remote processing and display workstation where the signal is digitized and processed to produce an mage that is then viewed on a display screen.

Also known, according to U.S. Pat. No. 5,912,942, is a type of x-ray detector wherein an active pixel sensor (APS) uses CMOS manufacturing technology.

In the above-mentioned patent, the radiology equipment described therein comprises:
- a source of x-rays passing through an object,
- a scintillator that converts the x-rays that have passed through the object into visible light,
- possibly, a fiber optic plate transmitting the converted visible light to an active pixels array (detector) that converts it into an analog electrical signal.

In this patent, it is explained that the signal can be converted into a digital signal in the sensor itself or in an interface case separate from the sensor and remote from the image signal processing and display unit.

In the dental radiological equipment that has just been described, it is not known whether the x-ray dose used to pass through a patient's tooth is sufficient to produce a good quality image on the display screen (correct exposure level), whether the dose is insufficient (under-exposure) or even excessive (over-exposure).

In some cases, a particularly experienced user can, by examining the screen image of the tooth, assess whether the patient has been exposed to too high a dose of x-rays and thus adjust the equipment for future image taking.

However, this is not something most users can do, as they do not always know how to analyze the tooth image reliably.

SUMMARY OF THE INVENTION

Given the above, it would therefore be useful to be able to control, at least partially, the x-ray exposure levels that patients are subject to, to prevent them being continuously exposed to unsuitable x-ray doses.

Therefore, the invention relates to a signal processing method in a dental radiology apparatus comprising an intraoral sensor that delivers at least one analog image output signal in response to an exposure of said sensor to x-rays, characterized in that it has the following steps:

- conversion of said at least one analog image output signal into one digital image output signal,
- processing of the digital image output signal to obtain a indication report of the x-ray exposure level that has been used to deliver said analog output signal, the indication report of the exposure level corresponding to an exposure level classified as under-exposure, correct exposure or over-exposure,
- supply of the indication report of the exposure level used.

In conjunction with this, the invention also targets a dental radiology apparatus comprising an intraoral sensor that is adjusted to deliver at least one analog image output signal, in response to an exposure of said sensor to x-rays, characterized in that it comprises:

- a conversion unit of said at least one analog image output signal into one digital image output signal,
- a processing unit of the digital image output signal that is adapted to obtain a report indicating the x-ray exposure level that has been used to deliver said analog output signal, the report indicating the exposure level corresponding to an exposure level qualified as under-exposure, correct exposure or over-exposure,
- means of supply of the report indicating the exposure level used.

Thus, by processing the digital output signal, it is possible to supply the user of the dental radiology apparatus according to the invention with a report indicating the x-ray exposure level the patient has just been subjected to, in order to indicate whether this was an insufficient, satisfactory or excessive exposure level.

According to the report indicating the exposure level used, it thus becomes possible to adapt the exposure level of the x-ray sensor for later analog image output signals.

Thus the invention makes the dental radiology apparatus used safer for patients than before insofar as any high x-ray doses which patients are subject to can be detected more easily than before.

Furthermore, the invention enables easier adjustment of the dental radiology apparatus than before, as the user is automatically informed of the exposure level used.

According to one characteristic, the processing of the digital image output signal is performed based on the extreme amplitude values of said signal that were previously determined, in order to optimize the useful range of variation of the digital data according to the effective variation range of the signal's analog data.

According to one characteristic, the processing includes the following steps:
- comparison of one extreme amplitude value or a combination of extreme amplitude values with one or more threshold values,
- according to the result of the comparison(s), supply of the report indicating the exposure level used.

By ensuring that the amplitude of variation of the analog signal corresponds with a wide enough variation range of the digital data, and thus by adapting the x-ray dose emitted, the amplitude of the digital data is maximized, thus improving the conversion's signal-to-noise ratio by limiting the noise of said digital-analog conversion.

According to one characteristic, the processing first includes a step of forming a curve giving the number of pixels of the image signal per gray level.

This curve, or image histogram, enables the variation range of the digital data to be determined.

According to one characteristic, the processing includes a step of determining the extreme amplitude values (max, min) of the curve's gray levels.

According to one characteristic, the processing includes a step of determining a difference $\Delta=\max-\min$.

This difference $\Delta$ gives the range of variation of the digital data and is sufficient to determine the exposure level used and, thus, supply useful information to the user.

According to one characteristic, the processing includes a first step of comparison of the difference $\Delta$ with a first value threshold1.

According to one characteristic, the processing includes a decision step as to the supply of the report indicating the exposure level used or as to the performance of a second comparison step according to the result of the first comparison step.

According to one characteristic, the report indicating the exposure level used corresponds to an under-exposure level when the difference $\Delta$ is less than or equal to the first value threshold1.

When the x-ray exposure level is low, the analog signal is low and thus the variation range of the digital data is reduced.

According to one characteristic, when the difference $\Delta$ is greater than the first value threshold1, then the processing includes a second step of comparison of the max value with a second value threshold2.

According to one characteristic, the processing includes a decision step as to the supply of the report indicating the exposure level used or as to the performance of an additional test, according to the result of the second comparison step.

According to one characteristic, the report indicating the exposure level used corresponds to a correct exposure level when the max value is less than the second value threshold2.

This max value is representative of the pixels having received the most x-rays. When this value approaches the max value of the digital data, the max value of the x-ray dose that corresponds to the saturation of the signal processing chain is approached, thus indicating image over-exposure.

According to one variant, the difference $\Delta$ is compared with a value threshold3 in order to detect over-exposure. This variant is particularly useful for an image having a large number of gray levels and which, for example, has been produced on a relatively heterogeneous object from the point of view of radiological densities.

According to one characteristic, when the maximum value is greater than or equal to the second value threshold2, then the processing includes an additional test step in order to determine the presence or absence of data indicating an overflow in the digital output signal.

According to one characteristic, according to the determination of the presence or absence of data indicating an overflow, the processing includes a decision step as to the supply of the report indicating the exposure level used corresponding respectively to an over-exposure level or a correct exposure level.

This additional step avoids any variations in the analog signal amplitude from one sensor to another. The amplitude of analog signal variation ideally corresponds to the variation amplitude of the digital data, called input window of the analog-digital converter. It is desirable through design to ensure that the variation amplitude of the analog signal is not less than the window of the analog-digital converter, in order to take full advantage of the variation ranges of the digital data. Conversely, where the variation amplitude of the analog signal may, for a given sensor, exceed the window of the analog-digital converter, the data indicating an overflow (overflow bit) also supply an indication of saturation of the signal processing chain.

According to one characteristic, the method includes a display step of the report indicating the exposure level used on a display screen.

According to one characteristic, the method includes a display step of the corresponding image signal on the display screen.

According to one characteristic, the report indicating the exposure level is displayed in the form of at least one indicator whose position varies according to the report obtained by the signal processing and, for example, according to the difference $\Delta$ obtained.

Advantageously, but not exclusively, this indicator can be displayed in the form of a linear cursor.

According to one characteristic, the report indicating the level of under-exposure, correct exposure or over-exposure is displayed in the form of a cursor producing a visual effect that varies at least for certain exposure levels.

Thus a critical exposure level can rapidly be detected from a normal exposure level.

For example, the visual effect is color.

According to one characteristic, the conversion step is performed in an analog-digital converter having an input window adapted to the dynamic range of the analog signal delivered by the sensor.

BRIEF DESCRIPTION OF THE DRAWINGS

Other characteristics and advantages will appear during the following description, given solely as a non-limiting example and with reference to the appended drawings, wherein.

DETAILED DESCRIPTION OF THE INVENTION

Figure 1:
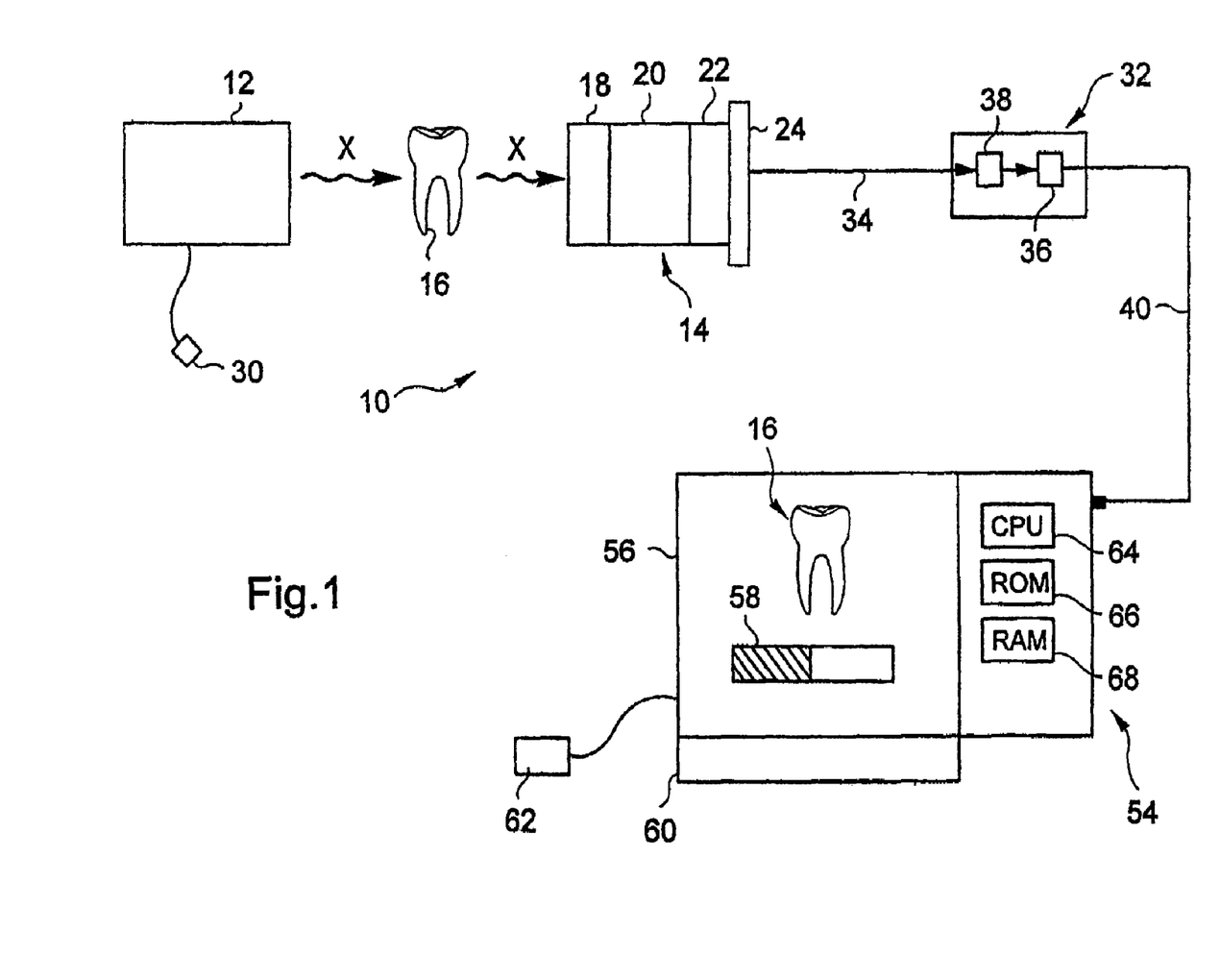
FIG. 1 is a overall schematic view of the dental radiology apparatus according to the invention, during the taking of an image of a tooth.

As represented in FIG. 1, an x-ray dental radiology apparatus 10 comprises an x-ray source 12 placed outside a patient's mouth and an intraoral radiation sensor 14 arranged in a patient's mouth, behind a tooth 16, and which is capable of receiving the x-rays that have passed through the tooth.

The sensor 14 comprises, in the propagation order of the radiation, a scintillator 18 that converts the x-rays that have passed through the tooth into visible light, possibly a fiber optic plate that, on the one hand, includes metal particles intended to absorb the part of the x-rays received by the scintillator and not converted into visible light and, on the other hand, conducts the visible light thus converted to a detector 22. This detector is mounted on a ceramic substrate 24 and converts the visible radiation from the optical fibers into one or more analog electrical signals.

It may be noted that other sensor structures can be suitable including, for example, a sensor with a scintillator directly arranged against the detector.

The various components of the sensor 14 are assembled together, for example, by gluing.

The scintillator 18 is, for example, made from gadolinium oxysulfide.

Alternatively, it can be made from cesium iodide, lutetium crystals or any element having the property of converting x-rays into visible radiation.

The fiber optic plate 20 when present is, for example, marketed by SCHOTT with the commercial reference 47A or by HAMAMATSU with commercial reference XRS.

The detector 22 can be a charge-coupled device (CCD) type detector as used in French Patent FR 2,547,495 or European Patent No. 0,129,451.

This detector 22 can also, and in a non-limiting way, be an APS type detector (Active Pixel Sensor) using the CMOS manufacturing technology, as described in U.S. Pat. No. 5,912,942.

The apparatus also comprises an activation device 30 of the x-ray generator 12 in order to emit x-rays and possibly to adapt the x-ray dose. However, dose adjustment can be carried out otherwise and, for example, directly on the generator.

The radiology apparatus 10 comprises an electronic module 32 remote from the sensor 14 and thus from the detector 22 of FIG. 1, which is linked to this sensor by a wire link 34 that is a cable.

For example, the cable is of the multi-wire or multi-strand type, the high-frequency signals (clock, video, etc.) can optionally be the subject of coaxial cables with the assembly being shielded by a ground braid.

It may be noted that the electronic module mainly comprises an analog-digital converter 36 and a unit 38 for amplifying and filtering before conversion.

The radiology apparatus 10 also includes a processing and display unit 54 remote from the electronic module 32 and linked to the latter by means of a wire link 40 which is, for example, a cable.

The processing and display unit 54 is, for example, a computer that receives the sensor 14 output signals, once digitized in the electronic module 32, in order to carry out on the latter appropriate image processing that is known to those skilled in the art to view on the screen 56 the image of the tooth 16 of FIG. 1.

It may be noted that the conversion can alternatively be performed directly in the unit 54 and, in this case, module 32 is done without.

An interface in compliance with standard USB2.0 is provided at the output of unit 32, and a USB2.0 serial bus and an corresponding interface in the remote computer (not shown), so that the signals delivered by the module 32 are transmitted to the remote computer 54 at high speed, for example about 480 mbps.

The use of such an interface thus enables the high speed transmission to the computer of data that are supplied by the detector 22 and processed by the module 32.

The use of this interface is particularly well-suited to the use of a high frequency clock signal, for example 12 MHz, for sampling the data collected by the detector 22, that is without having to use a buffer memory to store the data before their transmission to the computer.

Indeed, this clock signal frequency represents a good compromise between, on the one hand, too low a frequency to sample the detector, which would cause an increase of the dark current between the start and end of the detector sampling and, on the other hand, too high a frequency which would generate additional reading noise disturbing the detector's output signal.

Indeed, given the constraints linked to dark current development in the detector over time, the detector's pixels have to be sampled at a relatively high frequency, which can be incompatible with the transmission speed permitted by standard USB1.

It may be noted that the data transmission speed on the wire link 40 has to be at least equal to that provided by standard USB2.0 in order to be able to empty the detector 26 (for example an active pixel array) rapidly without having to make use of a buffer memory.

It should be noted that the analog-digital converter 36 has an input window that is adjusted to the dynamic range of the analog output signal delivered by the sensor 14 and, more particularly, by the detector 22, to prevent, in the case of too wide dimensioning of the window, the signal attacking the converter from ever saturating it.

The dimensioning of such a window can be obtained by a successive approach and by simple execution measures known to those skilled in the art.

For example, a converter is chosen that samples the analog output signal supplied to it at the input on 12 bits, and an input window width is adopted, for example, of 2 volts.

This means that for a 0-volt signal at input, a converter output value of 0 is obtained and for a 2-volt input signal, an output value of 4095 is obtained.

If the input signal is, for example, 2.1 volts, then a value of 4095 is obtained at the converter output as well as, in the digital output signal, data (bit) indicative of an overflow indicating saturation.

It may be noted that converters sampling on a different number of bits can be used as part of the invention.

The processing and display unit 54 comprises, as seen above, the screen 56 on which the image signal of the tooth 16 is displayed or viewed, as well as at least one indicator (cursor or progress bar) 58 represented on the screen 56 under the image of the tooth.

As will be seen later, the position of this indicator (for example a cursor) is representative of an exposure level of the sensor 14 to the x-rays used (dose received by the patient) to deliver the relevant analog output signal.

Other indicators or interface elements can, of course, be used to supply the user of the dental radiology apparatus with a report indicating the exposure level to the x-rays used.

The unit 54 also comprises a keyboard 60 and an input interface such as a mouse 62.

Furthermore, the unit 54 comprises a central processing unit 64, a ROM 66 and RAM 68.

Figure 2:
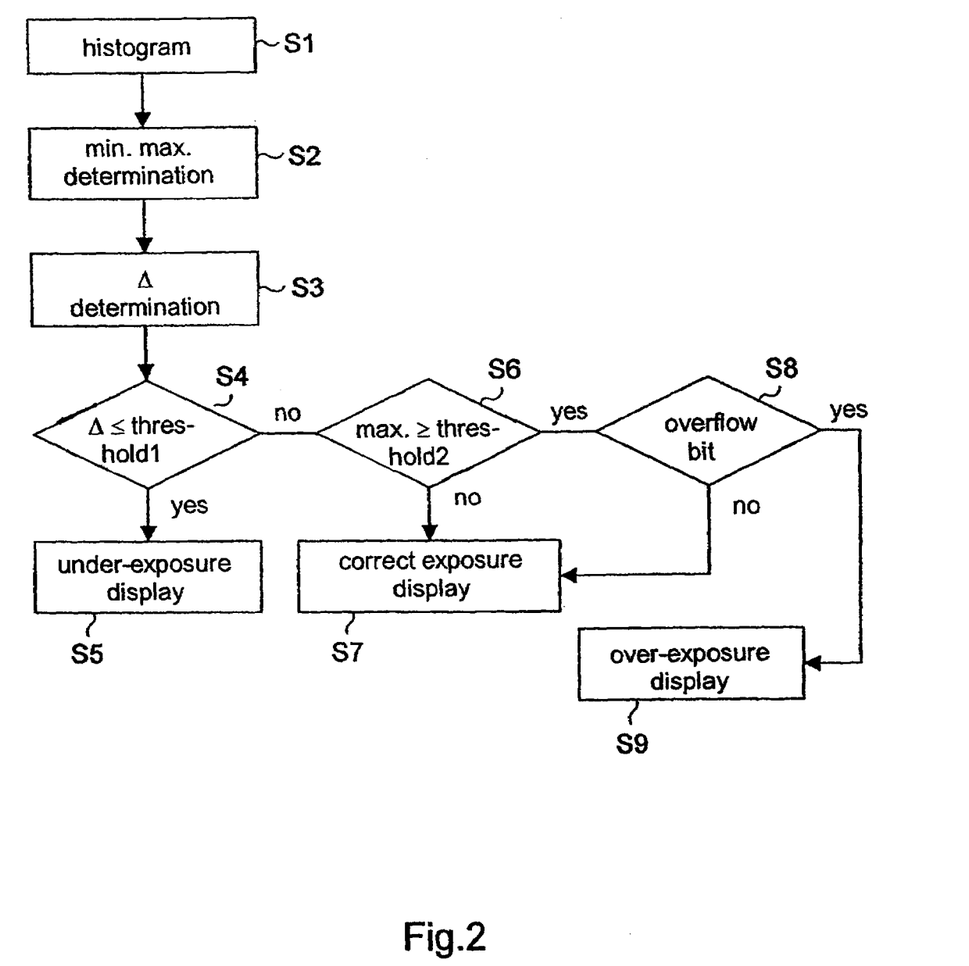
FIG. 2 is a view of an algorithm of a computer program executed in the central processing unit of FIG. 1.

A computer program whose algorithm is represented in FIG. 2 is stored in the memory 66 and, when the system is initialized, loaded into the memory 68 and then executed by the central processing unit 64.

The algorithm of FIG. 2 comprises a series of steps corresponding to the instructions or portions of code of a program that, once executed by the unit 54, will enable the method according to the invention to be implemented.

Figure 3:
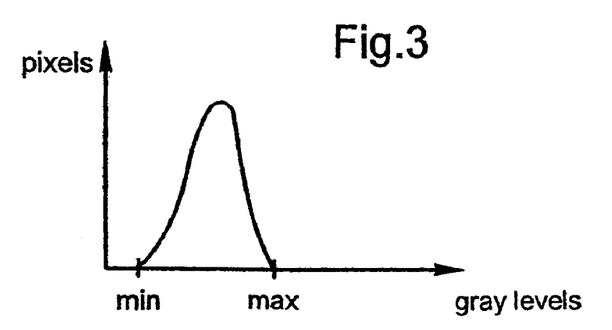
FIG. 3 is a schematic view illustrating a histogram giving the number of pixels of the image signal according to the gray levels.

The algorithm of FIG. 2 comprises a first step S1 during which the histogram of the digital output signal is determined that conveys, as represented in FIG. 3, the number of pixels given per digital gray level in the digital image output signal.

In FIG. 3 for the relevant histogram, an extreme minimum amplitude gray level value (minimum value) and an extreme maximum amplitude gray level value (maximum value) will thus be seen to appear.

The histogram is conveyed in the form of a table of $2^n$ elements, i.e. 4096 in the selected example with a converter sampling at 12 bits.

During the next step S2, the extreme amplitude signal values are determined (in terms of gray levels in the histogram of FIG. 3) in the digital signal, and more particularly in the histogram, i.e. the above-mentioned minimum and maximum values.

To do this, the table of 4096 elements, whose width is that of the histogram, is looked up to determine, on the one hand, the smallest non-zero value of the table (min) and, on the other hand, the largest non-zero value of the table (max).

It may be noted that production of the histogram of FIG. 3 corresponds to a statistical processing of the image signal per gray levels which is known to those skilled in the art.

During the next step S3, the difference Δ is determined between the maximum value and the minimum value determined by the previous step.

Based on this difference, one is already capable of determining the position of the cursor illustrated in the figures.

The algorithm then comprises a first step S4 of comparison of the difference Δ with a first threshold value called threshold1 and which is, for example, set to the value 256.

This value indicates an insufficient dose of x-rays (exposure level classified as under-exposure).

According to the result of this comparison step, a decision can be taken as to the supply of the report indicating the exposure level used when taking the image or as to the performance of a second comparison step.

Thus, if the difference Δ is less than or equal to the value threshold1, then the step S4 is followed by a step S5 which aims to supply the user with the report indicating the exposure level used to take the relevant image.

The report indicating the exposure level used here corresponds to an under-exposure which is displayed on the display screen.

Figure 5A:
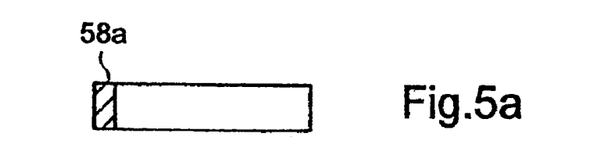
FIGS. 5a, 5b, 5c illustrate respectively three possible cursor positions represented in FIG. 1 for the various histograms illustrated in FIG. 4.

The corresponding position of the cursor 58 for an insufficient exposure level (under-exposure) is represented in FIG. 5a and is identified by a small zone 58a on the left-hand side.

When the cursor is in this position, the user is informed that an insufficient dose of x-rays has been used to take the image of the patient's tooth and the resulting image is thus underexposed.

The dose of x-rays should thus be increased for the next image taking.

Figure 4:
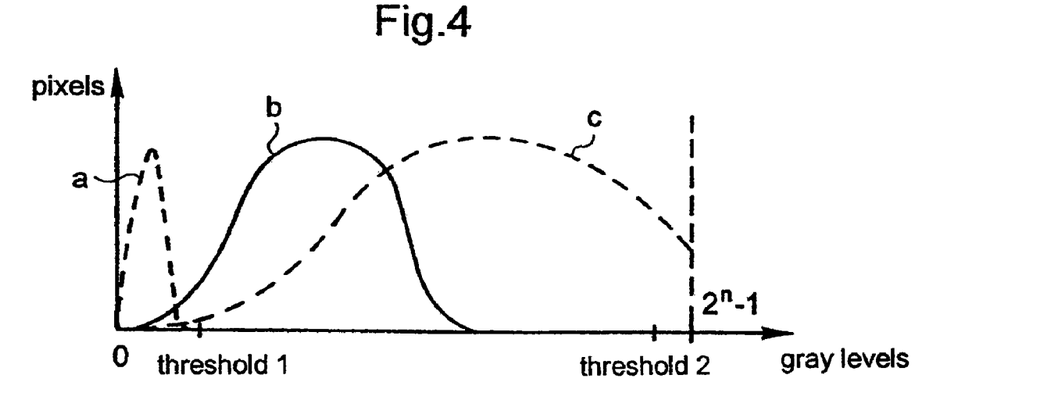
FIG. 4 illustrates three histograms of image output signals corresponding respectively to three exposure levels of the sensor to x-rays.

This phenomenon is illustrated in FIG. 4 by the histogram marked a.

It may be noted that the value $2^n-1$ represents the amplitude of the output window of the converter used which, in the example described, is set to 4095 (12-bit signal).

When the difference Δ is greater than the first value threshold1, then the signal processing of the algorithm of FIG. 2 involves a second comparison step S6 during which the maximum value is compared with a second value threshold2 that is chosen, for example, so as to be near the value $2^n-1$ of FIG. 4. This threshold value is, for example, set to $2^n-1-$threshold1 in the considered example, i.e. here 4095-256.

The comparison of the maximum value at this value threshold2 near the edge of the converter's output window will enable an indication to be supplied on the exposure level used.

Indeed, when the maximum value is strictly less than the value threshold2, then it is decided to supply the user with the report indicating the exposure level used that corresponds to a correct exposure and display this report indicating the exposure level on the screen 56 of FIG. 1.

This case corresponds to a satisfactory dose of x-rays that will not require adjustment of the apparatus of FIG. 1 and more particularly the x-ray source 12 (modification of the x-ray dose).

Figure 5B:
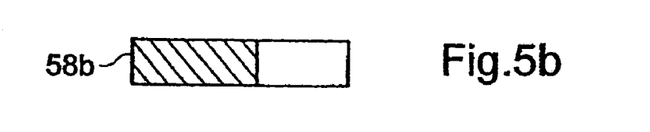

The corresponding exposure level is shown by the position of the cursor 58b in FIG. 5b.

To clearly identify the positions of the two respective cursors of FIGS. 5a and 5b, one can, for example, represent the cursor 58a in red and the cursor 58b in green or use any another visual effect enabling the two cursors to be identified one from the other and thus differentiate the two exposure levels.

It may be noted that FIG. 5b supplies in the form of a display the report indicating the exposure level used to produce an output signal whose histogram is that marked b in FIG. 4.

When the maximum value is greater than or equal to the preset value threshold2, the step S6 is followed by a step S8 during which a test is performed to determine whether the data indicating an overflow are present in the digital output signal supplied by the converter.

These data are, for example, in the form of an overflow bit whose presence is representative of an input signal whose dynamic range is greater than that of the converter's input window.

When such a value indicating an overflow is absent from the signal, then the step S8 is followed by the previously described step S7.

This case corresponds to a histogram whose rate is that of the histogram marked b on FIG. 4 and whose report indicating the exposure level used is illustrated in FIG. 5b.

However, in this case, the maximum value of the histogram b is between the value threshold2 and the value $2^n-1$.

On the contrary, when the presence of a value indicating an overflow is detected in the digital signal, then the step S8 is followed by a step S9 which involves supplying the user with the corresponding report indicating the exposure level used.

Here, the exposure level used corresponds to an over-exposure, which means that the dose of x-rays used to take the image of the viewed tooth was excessive.

Figure 5C:
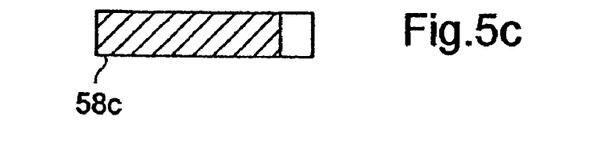

The report indicating the exposure level used in FIG. 5c is given by the position of the cursor 58c that occupies almost all the rectangle.

It may be noted that to distinguish this case from that of FIG. 5b, one can, for example, represent the cursor 58c in red, the cursor 58b being represented in green, or even use another visual effect (different cursor patterns, modification of the cursor dimensions, another element appearing on the screen, etc.).

An audible indicator in addition to or in place of the visual indicator can also be used.

The position of the cursor in FIG. 5c supplies the report indicating the exposure level to x-rays used to produce an output signal from the sensor whose histogram is that marked c in FIG. 4.

It may be noted that in the extreme cases represented by the curves a and c illustrated in FIGS. 5a and 5c, the supply to the user of the apparatus of the report indicating the corresponding exposure level used enables the user to adjust the apparatus accordingly.

Thus, in the case of under-exposure, he/she will increase the dose of x-rays for the next patient and, in case of over-exposure, he/she will decrease the dose of x-rays.

The invention thus enables, very easily and automatically, the detection of whether the image is over-exposed or under-exposed and thus whether the doses of x-rays used were dangerous or not for the patient without having to examine the image of the tooth produced on the screen 56.

Indeed, the information on the report indicating the exposure level used that is supplied to the user is particularly useful to the user who does not always know how to determine the exposure level by viewing the image of the tooth on the screen.

It is worth noting that the algorithm of FIG. 2 could be completed, for example, by adding steps of comparison with other threshold values so as to give the user more detailed information.

The user also saves precious time by having available unambiguous information that is not liable to reading error, which makes the invention particularly efficient and the apparatus reliable.

It may also be noted that the display of the report indicating the exposure level used to produce an image signal of a tooth can be done at the same time as the display of the image signal itself, as illustrated in FIG. 1.

The invention claimed is:

1. A signal processing method in a dental radiology apparatus comprising:
   converting at least one analog image output signal into one digital image output signal;
   processing the digital image output signal, wherein the processing comprises, forming a curve giving the number of pixels of the digital image output signal per gray level, and determining the extreme amplitude values (max, min) of the curve's digital gray levels to obtain a report indicating an x-ray exposure level that has been used to deliver said analog image output signal, and wherein the report indicating the exposure level corresponds to an exposure level classified as under-exposure, correct exposure or over-exposure; and
   supplying the report indicating the exposure level used.

2. The method according to claim 1, wherein the processing of the digital image output signal is based on extreme amplitude values of the digital image output signal that have been previously determined.

3. The method according to claim 2, wherein the processing further comprises:
   comparing one extreme amplitude value or a combination of extreme amplitude values with one or more threshold values; and
   supplying the report indicating the exposure level used.

4. The method according to claim 1, wherein the processing further includes determining a difference Δ=max-min.

5. The method according to claim 4, wherein the processing further includes a comparing the difference Δ with a first value threshold1.

6. The method according to claim 5, wherein the processing further includes performing a second comparison step according to the result of the first comparison step.

7. The method according to claim 6, wherein the report indicating the exposure level used corresponds to an under-exposure level when the difference Δ is less than or equal to the first value threshold1.

8. The method according to claim 6, wherein when the difference Δ is greater than the first value threshold1, then the processing further includes comparing the maximum value with a second value threshold2.

9. The method according to claim 5, wherein the report indicating the exposure level used corresponds to an under-exposure level when the difference Δ is less than or equal to the first value threshold1.

10. The method according to claim 5, wherein when the difference Δ is greater than the first value threshold1, then the processing further includes comparing the maximum amplitude value with a second value threshold2.

11. The method according to claim 10, wherein the processing further includes performing an additional test according to the result of the second comparison step.

12. The method according to claim 11, wherein the report indicating the exposure level used corresponds to a correct exposure level when the maximum value is less than the second value threshold2.

13. The method according to claim 11, wherein when the maximum amplitude value is greater than or equal to the second value threshold2, the processing further includes determining the presence or absence of data indicating an overflow in the digital output signal.

14. The method according to claim 10, wherein the report indicating the exposure level used corresponds to a correct exposure level when the maximum amplitude value is less than the second value threshold2.

15. The method according to claim 10, wherein when the maximum value is greater than or equal to the second value threshold2, the processing further includes determining the presence or absence of data indicating an overflow in the digital output signal.

16. The method according to claim 15, wherein according to determining the presence or absence of data indicating an overflow, the processing further includes deciding if the report indicating the exposure level used corresponds respectively to an over-exposure level or a correct exposure level.

17. The method according to claim 16, wherein the supplying further includes displaying the report indicating the exposure level used on a display screen.

18. The method according to claim 1, wherein the supplying further includes displaying the report indicating the exposure level used on a display screen.

19. The method according to claim 18, wherein the displaying further includes displaying the corresponding image signal on the display screen.

20. The method according to claim 18, wherein the report indicating the exposure level is displayed in the form of at least one indicator whose position varies according to the report obtained by the signal processing.

21. The method according to claim 20, wherein the position of the indicator varies according to the difference Δ obtained.

22. The method according to claim 21, wherein the report indicating the level of under-exposure, correct exposure or over-exposure is displayed in the form of a cursor producing a visual effect that varies at least for certain exposure levels.

23. The method according to claim 18, wherein the report indicating the level of under-exposure, correct exposure or over-exposure is displayed in the form of a cursor producing a visual effect that varies at least for certain exposure levels.

24. The method according to claim 23, wherein the visual effect is color.

25. The method according to claim 24, wherein the converting is performed in an analog-digital converter having an input window adjusted to the dynamic range of the analog signal delivered by the intraoral sensor.

26. The method according to claim 1, wherein the converting is performed in an analog-digital converter having an input window adjusted to a dynamic range of the analog signal delivered by an intraoral sensor.

27. A dental radiology apparatus comprising:
   an adjustable intraoral sensor configured to deliver at least one analog image output signal in response to an exposure of said adjustable intraoral sensor to x-rays;
   a conversion unit configured to convert at least one analog image output signal into one digital image output signal;
   a processing unit configured to form a curve giving the number of pixels of the digital image output signal per gray level, to determine extreme amplitude values (max, min) of the curve's digital gray levels, and to obtain a report indicating the x-ray exposure level that has been used to deliver said analog output signal, wherein the report indicating the exposure level corresponds to an exposure level classified as under-exposure, correct over-exposure; and means for supplying the report indicating the exposure level used.

28. The apparatus according to claim 27, wherein the processing unit comprises means for comparing that are adjusted to compare one extreme amplitude value or a combination of extreme amplitude values with one or more threshold values.

29. The apparatus according to claim 27, wherein the central processing unit comprises means for determining a difference $\Delta$=max-min.

30. The apparatus according to claim 29, wherein the central processing unit comprises means for comparing the difference $\Delta$ with a first value threshold1.

31. The apparatus according to claim 30, wherein the central processing unit further includes means for deciding to supply the report indicating the exposure level used or to perform a second comparison step according to the result supplied by the first means of for comparing.

32. The apparatus according to claim 31, wherein the report indicating the exposure level used corresponds to an under-exposure level when the difference $\Delta$ is less than or equal to the first value threshold1.

33. The apparatus according to claim 31, wherein the central processing unit further comprises second means for comparing the maximum amplitude value with a second value threshold2 that is adjusted to be implemented when the difference $\Delta$ is greater than the first value threshold1.

34. The apparatus according to claim 30, wherein the report indicating the exposure level used corresponds to an under-exposure level when the difference $\Delta$ is less than or equal to the first value threshold1.

35. The apparatus according to claim 30, wherein the central processing unit further comprises a second means for comparing the maximum amplitude value with a second value threshold2 that is adjusted to be implemented when the difference $\Delta$ is greater than the first value threshold1.

36. The apparatus according to claim 35, wherein the central processing unit further comprises means for deciding to the supply of the report indicating the exposure level used or the performance of an additional test, according to the result supplied by the second means for comparing.

37. The apparatus according to claim 36, wherein the report indicating the exposure level used corresponds to a correct exposure level when the maximum value is less than the second value threshold2.

38. The apparatus according to claim 36, wherein the central processing unit further comprises means for determining the presence or absence of data indicating an overflow in the digital output signal when the maximum amplitude value is greater than or equal to the second value threshold2.

39. The apparatus according to claim 35, wherein the report indicating the exposure level used corresponds to a correct exposure level when the maximum amplitude value is less than the second value threshold2.

40. The apparatus according to claim 35, wherein the central processing unit further comprises means for determining the presence or absence of data indicating an overflow in the digital output signal implemented when the maximum amplitude value is greater than or equal to the second value threshold2.

41. The apparatus according to claim 40, wherein the central processing unit comprises means for deciding to supply the report indicating the exposure level used corresponding respectively to an over-exposure level or a correct exposure level, according to the determination of the presence or absence of data indicating an overflow.

42. The apparatus according to claim 41 wherein the means for supplying further comprises means for displaying the report indicating the exposure level used on a display screen.

43. The apparatus according to claim 27, wherein the means for supplying further comprises means for displaying the report indicating the exposure level used on a display screen.

44. The apparatus according to claim 43, wherein the means for displaying displays the corresponding image signal on the display screen.

45. The apparatus according to claim 43, wherein the report indicating the exposure level is displayed in the form of at least one indicator whose position varies according to the report obtained by the signal processing.

46. The apparatus according to claim 45, characterized in that wherein the position of the indicator varies according to the difference $\Delta$ obtained.

47. The apparatus according to claim 46, wherein the report indicating the level of under-exposure, correct exposure or over-exposure is displayed in the form of a cursor producing a visual effect that varies at least for certain exposure levels.

48. The apparatus according to claim 43, wherein the report indicating the level of under-exposure, correct exposure or over-exposure is displayed in the form of a cursor producing a visual effect that varies at least for certain exposure levels.

49. The apparatus according to claim 48, wherein the visual effect is color.

50. The apparatus according to claim 49, further comprising an analog-digital conversion unit having an input window adjusted to the dynamic range of the analog signal delivered by the sensor.

51. The apparatus according to claim 27, further comprising an analog-digital conversion unit that has an input window adjusted to the dynamic range of the analog signal delivered by the sensor.

* * * * *

UNITED STATES PATENT AND TRADEMARK OFFICE
CERTIFICATE OF CORRECTION

PATENT NO. : 7,711,173 B2  Page 1 of 1
APPLICATION NO. : 10/595985
DATED : May 4, 2010
INVENTOR(S) : Jean-Marc Inglese

It is certified that error appears in the above-identified patent and that said Letters Patent is hereby corrected as shown below:

Column 11, claim 27, line 3      Please insert --exposure or-- after "correct"

Column 12, claim 46, lines 31-32      Please delete "characterized in that"

Signed and Sealed this

First Day of June, 2010

David J. Kappos
*Director of the United States Patent and Trademark Office*